United States Patent [19]

Metzenberg et al.

[11] 4,166,766

[45] Sep. 4, 1979

[54] METHOD FOR QUANTITATIVE ASSAY OF ALKALINE PHOSPHATASE ISOENZYMES IN SERUM

[75] Inventors: Robert L. Metzenberg; Frank C. Larson; Lawrence Kahan, all of Madison, Wis.

[73] Assignee: Wisconsin Alumni Research Foundation, Madison, Wis.

[21] Appl. No.: 712,879

[22] Filed: Aug. 9, 1976
(Under 37 CFR 1.47)

[51] Int. Cl.$^2$ ............................................. G01N 33/16
[52] U.S. Cl. ........................................ 435/21; 435/815
[58] Field of Search ...................... 195/103.5 R, 66 R

[56] References Cited

U.S. PATENT DOCUMENTS 4,030,995  6/1977  Starkweather ............... 195/103.5 R

*Primary Examiner*—Alvin E. Tanenholtz
*Attorney, Agent, or Firm*—McDougall, Hersh & Scott

[57] ABSTRACT

A method of assay for fast electrophoretic mobility alkaline phosphatase isoenzyme variant in serum comprising the steps of first separating the fast electrophoretic mobility alkaline phosphatase isoenzyme variant from the serum and from slower mobility isoenzymes and then measuring the activity of the separated fast isoenzyme variant and in which the determined activity can be used to indicate the presence of cancer and the direction of progress of cancer cure.

7 Claims, No Drawings

METHOD FOR QUANTITATIVE ASSAY OF ALKALINE PHOSPHATASE ISOENZYMES IN SERUM

This invention relates to a quantitative assay of alkaline phosphatase isoenzymes in serum, which finds use in providing a clue to the presence of a number of various forms of cancer and for determination of the progress being achieved during treatment of a patient having cancer.

A great deal has been published on tests for the presence of cancer wherein a small increment of a patient's blood has been analyzed for the presence of tumor-associated proteins, such as carcino-embryonic antigen (CEA) in colorectal cancer, alpha fetoprotein ($\alpha$ FP) in hepatic cancer, and the placental (Regan or Nagao) alkaline phosphatase isoenzymes in gynecological cancer. The usefulness of these proteins in both initial diagnosis and evaluation of the progress in the treatment of cancer is limited by the fact that they occur with low frequency in all human beings, including the healthy, and/or they have been found to be indicative of only a limited variety of cancers. In addition, the assay for CEA or $\alpha$ FP is difficult, time consuming and expensive and useful primarily as a means of monitoring the progress of therapy.

It is believed that a more reliable diagnosis for cancer, especially in its early stages, and for the progress of cure in its later stages, requires the ability to effect a qualitative separation from the blood or serum of a component secreted by various of the types of tumors followed by a quantitative evaluation of the separated component for purposes of comparison with normal levels of activity. Such diagnosis is more reliable for the early detection of cancer and it offers a more reliable test for determining the progress during treatment of a cancer patient.

It has been found, in accordance with the practice of this invention, that a fast electrophoretic mobility variant alkaline phosphatase isoenzyme occurs in the serum in patients with cancer of various types. The cancers include a wide variety of cell types, location and stage of tumor development. The variant can be easily separated by ion exchange chromatography, and once the isoenzyme has been isolated it becomes possible to make a quantitative evaluation to determine the level of activity, thereby to provide a more reliable diagnosis for the presence of cancer and the course of cancer treatment.

The occurrence of the isoenzyme variant is common in the serum of patients having diabetes mellitus (about 64%), but present only in less than 10% of presumably healthy human beings. Detection of the isoenzyme in patients known to have diabetes mellitus is not considered reason to suspect the existence of cancer in these patients.

The practice of this invention will hereinafter be described by way of separation of the isoenzyme variant from human serum by ion exchange column chromatography followed by analysis to determine the activity of the separated isoenzyme to determine the level in the human serum.

Separation of human serum alkaline phosphatase isoenzyme variant by ion exchange column chromatography:

EXAMPLE 1

Preparation of the ion exchange medium

To 5 grams diethyl aminoethyl (DEAE) ion exchange resin in the form of cross linked dextran (Sephadex A50), addition is made with stirring of 2 liters of a buffer formulated of 0.15 molar NaCl and 0.020 molar triethanolamine acetate.

The composition is allowed to stand over night at room temperature (23° C.). The buffer has a pH of 7.4 before addition to the exchanger.

The buffer is decanted from the resin and 2 liters of fresh buffer are added. This procedure is repeated two or more times, with the mixture being allowed to stand for several hours before addition of each new increment of buffer. This is an equilibrium procedure wherein the ion exchange resin in chloride form is equilibrated with the concentration of chloride in the buffer at pH 7.4.

EXAMPLE 2

Chromatrographic separation

A column containing 1.2 ml of gravity packed ion exchange resin from Example 1 is provided in a 3 ml syringe barrel from a 50% slurry of the ion exchange resin. A glass wool is used to plug the outlet from the barrel.

The packed column is washed with 10 ml of fresh buffer of the type previously described and the liquid level is allowed to drop to the top of the packed exchange column.

0.1 ml of the sample of human serum is applied and washed through the column with 6 to 10 ml of fresh buffer solution after which the buffer level is allowed to drop to the top of the ion exchange resin column. The fraction that is washed through will contain primarily the slow isoenzymes such as normal liver enzyme, bone and intestinal enzyme, while the fast electrophoretic variant alkaline phosphatase isoenzyme is still retained on the ion exchange resin.

Release of the fast electrophoretic variant alkaline phosphatase isoenzyme from the ion exchange resin is effected by contact of the ion exchange resin with a solution containing a higher concentration of NaCl. For this purpose, the ion exchange resin column is washed with 4 ml of an aqueous solution having a pH of 7.4, containing 0.4 molar NaCl and 0.02 molar triethanolamine acetate. The eluant fraction, which is collected, contains the fast electrophoretic variant alkaline phosphatase isoenzyme.

The concentration of NaCl can be varied in the eluant solution. For example, the variant can be removed from the ion exchange resin with a wash containing 0.15 mole NaCl but only when use is made of an impractically large volume of wash solution. Best results are obtained when the concentration of NaCl exceed 0.2 M in the wash but preferably not more than 0.8 M. Within the preferred range of about 0.3 to 0.5 M, the variant is removed at a controllable rate with a minimum amount of contamination thereby to provide a sharp band in the subsequent electrophoresis evaluation. Under these conditions, a qualitative separation of slow and fast isoenzymes is achieved as measured by electrophoretic analysis of each fraction. At least 80% of the isoenzymes are recovered.

Instead of Sephadex, other well known anion exchange resins, such as DEAE-cellulose, or diethyl-(2-hydroxypropyl) amino ethyl Sephadex (QAE-Sephadex, can be used. Separation can be effected at a pH within the range of 6 to 9, but it is preferred to approximate blood pH at about 7.2 to 7.4 for carrying out the separation. By way of further modification, other salts can be used in preparation of the buffer depending somewhat on the pH.

Use can also be made of a column packed with a cation exchange resin, such as sulfopropyl Sephadex, but then the order of elution is reversed in that the fast variant alkaline phosphatase isoenxyme will be eluted from the resin phase, while the remainder comes off by washing with a buffer of either a higher pH or a higher ionic strength than that used to apply the sample.

Thus the pH range and the buffer composition will depend upon whether a cation or anion exchange resin is used.

EXAMPLE 3

Qualitative electrophoretic analysis

Buffer composition:

14.92 grams of triethanolamine are dissolved in 1950 ml of water and the pH is adjusted to pH 7.0 with glacial acetic acid. The solution is diluted with water to a volume of 2000 ml.

Agar plates:

Per plate, 22.5 ml of 2-amino-2-ethyl-1,3-propane diol (1.0 M, pH 9.9), 6.8 ml water, and 0.4 gram Agar (Bacto Agar) are combined and autoclaved for 20 minutes. After cooling to 60° C., 11.4 mg of 2-hydroxy-3-amido-N-(2',4'-dimethylphenyl) naphthyl phosphate (alpha naphthol AS-MX phosphate) is dissolved in the autoclaved mixture and the solution is poured into a 100 mm×100 mm×15 mm plastic petri dish and allowed to set.

Procedure:

The electrophoresis chamber, such as a Gelman De-Luxe electrophoresis chamber, having a capacity of about 1 liter, is prepared with cold buffer composition and allowed to equilibrate. For this purpose, large strips of cellulose polyacetate, of the type marketed under the name Sepraphore III cellulose polyacetate electrophoresis strips 1"×6.75"×0.005" thickness (Gelman) are presoaked in the triethanolamine buffer for 30 minutes prior to use. The strips are provided in each chamber and a potential of 250 volts is applied across the strips for 30 minutes prior to sample application.

A cellulose polyacetate strip (0.8"×0.05"×0.005") is dipped into the sample to be tested and excess is removed with blotting paper. The strip is placed on the cathode end of the equilibrated strip in the chamber. After all samples have been applied, the sample strips are allowed to remain on the equilibrated long electrophoresis strips for about 30 minutes without the application of any potential. This is to allow the samples from the smaller strips to diffuse into the larger equilibrated strips. The time can be varied over a fairly wide range, such as 20–30 minutes. The narrow band of sample, which will be at right angles to the direction of migration, represents the origin.

The small strips, originally containing the sample, are removed from the larger equilibrated strips. A potential of 350 volts is applied for 35–40 minutes. The time can be varied, depending somewhat upon the potential, such as 60 minutes at 250 volts. The larger strips are removed from the chamber and placed on an absorbent sheet and the strips are placed onto agar plates without allowing any excess buffer to run along the strip, otherwise the bands may be blurred. To reduce the strip length to less than 100 mm, the ends of the strips can be cut off, without removing the origin, before the strips are placed onto the agar plates.

The strips are incubated at room temperature for 20 minutes before evaluation under short wave length ultra violet light.

In the described electrophoresis test and in the automated analysis, a normal serum sample without variant and a known positive with variant are run simultaneously with the sample of the unknown for comparison and standardization.

Activity, indicative of the level of the variant in the serum, is measured on a Technicon Autoanalyzer having the configuration shown in the accompanying figure.

A substrate having the following formulation is run at 1.2 ml per minute with the sample, in the form of column fractions derived from the eluant from the ion exchange separation run, at the rate of 0.32 ml per minute, making a total rate through the double mixing coil of 1.52 ml per minute. The substrate is formulated to contain 1.14 molar 2-amino-2-methyl-1-propanol. HCl, 0.60 mM α-naphthol AS-MX phosphate, and 0.25 mM MgCl$_2$, all dissolved in aqueous medium.

The activity of the alkaline phosphatase in serum was then calculated in accordance with the following equation:

$$\frac{\text{(fluorescence sample)} - \text{(Column Buffer Blank)}}{\text{fluorescence of 20 } \mu M \text{ Napthol AS-MX Standard}} \times$$
$$\frac{20 \, \mu M}{10 \, \text{min}} \times \frac{\text{Column Fraction Volume}}{\text{Serum Sample Volume}} \times$$
$$\text{Applied to Column}$$
$$\frac{1 \, \text{International Unit}}{\mu M \, \text{min}^{-1}} =$$

Units of Alkaline Phosphatase Activity
(One unit = 1 μ mole per min per liter)

20 column separations were performed on a sample of pooled sera from patients known to have the fast electrophoretic alkaline phosphatase variant isoenzyme. The calculated mean recovery from the columns was 85%. The assay had a coefficient of variation (percentage from standard deviation) of ±5%. This gives a confidence limit of ±10% for the assay.

The eluant from eight of the samples were analyzed electrophoretically and no cross contamination of isoenzymes was detected after 30 minute staining period.

Positive samples gave two fluorescent bands, the variant isoenzyme migrating further toward the anode than the band which corresponds to the band in the normal control sample.

The assays gave values for a standard serum of 191 International Units per liter.

As previously pointed out, instead of making use of anion exchange medium for separation of isoenzymes of alkaline phosphatase, use can be made of a cation ion exchange medium system wherein the variant isoenzyme is eluted from the ion exchange medium by the initial wash of the buffer therethrough, as illustrated by the following.

2 liters of 20 mM sodium succinate solution at a pH of 5.5 is added to 5 grams of Sulfopropyl Sephadex (dextran-based exchanger). The procedure for swelling and washing is the same as that of the previous example except that the succinate buffer is substituted for the NaCl/triethanolamine buffer.

3 μ units of Neuraminidase (H.C. 3.2.1.18 - Sigma type VI from Cl perfringens) is added to a 0.1 ml serum sample and incubated for 20 minutes at 37° C. 0.1 ml 10% acetic acid and 0.30 ml 20 mM sodium succinate buffer is added.

The sample is applied to a 1.5 ml ion exchange column packed with Sulfopropyl Sephadex. Elution is made with 10 ml of 0.04M NaCl and 20 mM sodium succinate buffer at pH 5.5. The fraction that comes off contains the fast electrophoretic enzyme variant and 0.4 ml 1M tris(hydroxymethyl)amino-methane (Trizma Base) is added to the eluted fraction.

The remainder, including the slow enzyme, is eluted from the column with 5 ml of 0.4M NaCl and 20 mM sodium succinnate at a pH of 5.5 and 0.2 ml of 1M Trizma Base is added.

The fractions are analyzed as described for alkaline phosphatase activity.

The foregoing procedure is useful not only for the diagnosis of cancer but of perhaps even more importance is its usefulness in following the treatment of cancer wherein reduction in calculated activity is indicative of effective treatment to reduce tumor growth, while increase in calculated activity would be indicative that the type of treatment that is being followed is not giving the desired effect and that a treatment change would be in order. The method of measurement is sufficiently rapid and reliable for beneficial use for evaluation of the success or failure of the course of treatment that is being followed. This cannot be done by present procedures which do not embody qualitative separation and quantitative determination by calculation of the activity of the separated variant.

The process described and claimed has application for the diagnosis and analysis for various forms of cancer including hepatomas, the latter of which has primarily dominated the earlier work on the early detection of cancer.

An important feature of this invention resides in the fact that analysis, combining separation and measurement of activity of the isolated variant, is made on serum without removal of protein since it is believed that the quantitative results depend upon the retention of all of the alkaline phosphatase protein in the whole serum. This is to be distinguished from procedures heretofore employed in analyses wherein methanol and ethanol fractions, containing the protein, are first removed.

The following tabulation indicates the results obtained in accordance with the practice of this invention on blood samples in which samples 661 to 677 were drawn at the University Hospitals, University of Wisconsin, while samples 802 to 811 were made available through the Red Cross. The values given in the column headed "Elect. Visual" represent three independent visual judgments from the electrophoresis test in which 0 indicates no fast isoenzyme while 3 indicates a maximum amount of fast enzyme.

The column headed "U/liter Fast" lists the values obtained in accordance with the practice of this invention of the amount of activity of the fast variant. It will be noted that there is good correlation between the activity measurements and the electrophoresis tests. Calculated activity below a value of 5 is believed to indicate that the patient is less likely to have cancer than a randomly selected person from the patient population, while a value of activity above 10 is indicative of the likely occurrence of cancer of any number of types. Values between 5 and 10 raise a red flag indicating that a thorough examination for other signs of cancer is appropriate and that frequent subsequent analyses should be made in order to follow the direction of movement of activity of the alkaline phosphatase variant value.

| Test No. | Elect. Visual | U/liter Fast |
|---|---|---|
| 661 | 1,1,1 | 7.6 |
| 662 | 0,1,0 | 1.9 |
| 664 | 2,2,2 | 8.0 |
| 665 | 1,0,1 | 5.7 |
| 667 | 0,0,0 | 4.2 |
| 668 | 3,3,3 | 212.4 |
| 669 | 0,0,0 | 2.4 |
| 671 | 0,0,0 | 8.0 |
| 673 | 1,1,1 | 2.4 |
| 676 | 2,2,2 | 11.8 |
| 677 | 2,2,2 | 4.7 |
| 802 | 0,0,0 | 2.4 |
| 803 | 0,0,0 | 2.4 |
| 804 | 1,1,0 | 4.2 |
| 805 | 0,0,0 | 2.8 |
| 806 | 0,0,0 | 6.1 |
| 807 | 0,0,0 | 7.6 |
| 808 | 1,2,0 | 6.6 |
| 809 | 0,0,0 | 2.4 |
| 810 | 0,0,0 | 3.3 |
| 811 | 0,0,0 | 1.4 |

We claim:

1. A method of assay for fast electrophoretic alkaline phosphatase isoenzyme variant in serum comprising first subjecting the serum to ion exchange chromatography to separate the fast isoenzyme variant mobility from slow isoenzyme variants s in the serum without prior removal of protein and measuring the activity of the separated fast isoenzyme variant.

2. A method of assay for fast electrophoretic alkaline phosphatase isoenzyme variant in serum comprising separating the fast isoenzyme variant mobility from slow isoenzyme variants in the serum without prior removal of protein, and measuring the activity of the separated fast isoenzyme variant, in which the first separation is effected by subjecting the serum to an ion exchange column, and then flushing the column with buffer for separation of the fast isoenzyme variant from the remainder.

3. The method as claimed in claim 2 in which the fast isoenzyme variant is flushed from the column with a buffer having a pH within the range of 6 to 9 and a concentration of salt above 0.15 M whereby the fast isoenzyme variant is removed for inclusion in the eluant.

4. The method as claimed in claim 3 in which the pH of the buffers is within the range of 7.2 to 7.4.

5. The method as claimed in claim 2 in which the ion exchange separation is effected with a cation exchange medium whereby the slow isoenzyme variants remain on the ion exchange medium for subsequent removal by a buffer having an ionic strength above that of the serum which is subjected to the ion exchange separation.

6. A method as claimed in claim 3 in which the buffer has a salt concentration within the range of 0.15 to 0.8 M.

7. A method as claimed in claim 3 in which the buffer has a salt concentration within the range of 0.3 to 0.5 M.

* * * * *